(12) United States Patent
Johnson

(10) Patent No.: US 11,147,946 B2
(45) Date of Patent: Oct. 19, 2021

(54) VENOUS ACCESS CATHETERS AND METHODS FOR PORTAL VENOUS SYSTEM CATHETERIZATION

(71) Applicant: THE REGENTS OF THE UNIVERSITY OF COLORADO, A BODY CORPORATE, Denver, CO (US)

(72) Inventor: Thor Johnson, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 19 days.

(21) Appl. No.: 15/516,618

(22) PCT Filed: Oct. 2, 2015

(86) PCT No.: PCT/US2015/053667
§ 371 (c)(1),
(2) Date: Apr. 3, 2017

(87) PCT Pub. No.: WO2016/054480
PCT Pub. Date: Apr. 7, 2016

(65) Prior Publication Data
US 2017/0319820 A1  Nov. 9, 2017

Related U.S. Application Data

(60) Provisional application No. 62/059,347, filed on Oct. 3, 2014.

(51) Int. Cl.
*A61M 25/00*  (2006.01)
*A61K 9/00*  (2006.01)
(Continued)

(52) U.S. Cl.
CPC ......... *A61M 25/0028* (2013.01); *A23L 33/15* (2016.08); *A23L 33/175* (2016.08);
(Continued)

(58) Field of Classification Search
CPC ............ A61M 25/0097; A61M 25/065; A61M 25/10; A61M 25/0028; A61M 25/0082;
(Continued)

(56) References Cited

U.S. PATENT DOCUMENTS 5,863,366 A * 1/1999 Snow ............... A61B 17/12022
156/143
6,287,290 B1 * 9/2001 Perkins ............. A61M 16/0486
604/516

(Continued)

OTHER PUBLICATIONS

Akagi et al., (2007) "Prevention of Catheter-Related Infections Using a Closed Hub System in Patients with Pulmonary Arterial Hypertension" *Circ. J.* 71(4):559-564.
(Continued)

*Primary Examiner* — Brandy S Lee
(74) *Attorney, Agent, or Firm* — Leason Ellis LLP

(57) ABSTRACT

The present invention contemplates devices and methods to administer nutritional compositions and/or therapeutic drugs directly into a portal venous system. For example, total parenteral nutrition therapy may be administered directly into the hepatic portal venous system thus circumventing known side effects of conventional parenteral administration. Alternatively, hepatic diseases and disorders may be treated using locally administered therapeutic drugs. Devices capable of direct portal venous system administration include, but are not limited to, a direct portal access catheter or a transjugular access catheter.

18 Claims, 4 Drawing Sheets

(51) Int. Cl.
| | |
|---|---|
| A23L 33/00 | (2016.01) |
| A23L 33/175 | (2016.01) |
| A23L 33/15 | (2016.01) |
| A61B 1/04 | (2006.01) |
| A61K 31/519 | (2006.01) |
| A61M 25/06 | (2006.01) |
| A61M 25/10 | (2013.01) |
| A61B 17/34 | (2006.01) |
| A61M 25/04 | (2006.01) |

(52) U.S. Cl.
CPC ............... *A23L 33/30* (2016.08); *A61B 1/04* (2013.01); *A61K 9/0029* (2013.01); *A61K 31/519* (2013.01); *A61M 25/0097* (2013.01); *A61M 25/065* (2013.01); *A61M 25/10* (2013.01); *A23V 2002/00* (2013.01); *A61B 17/3415* (2013.01); *A61M 25/0082* (2013.01); *A61M 25/04* (2013.01); *A61M 2025/1052* (2013.01)

(58) Field of Classification Search
CPC .......... A61M 25/04; A61M 2025/1052; A61M 25/01; A61B 17/3415; A61B 1/04; A61K 9/0029; A61K 31/519
See application file for complete search history.

(56) References Cited

U.S. PATENT DOCUMENTS

| | | | | |
|---|---|---|---|---|
| 2005/0020963 | A1* | 1/2005 | Gabal | A61F 2/04 604/8 |
| 2010/0249490 | A1* | 9/2010 | Farnan | A61M 25/005 600/16 |
| 2011/0213459 | A1* | 9/2011 | Garrison | A61F 2/013 623/2.11 |
| 2014/0257245 | A1* | 9/2014 | Rosenbluth | A61B 17/22032 604/509 |

OTHER PUBLICATIONS

Anthony et al., "Leucine stimulates translation initiation in skeletal muscle of postabsorptive rats via a rapamycin-sensitive pathway" *J Nutr.* (2000) 130(10): 2413-2419.
Behrens et al. (2012) "Transjugular Liver Biopsy" *Semin. Intervent. Radiol.* 29(2): 111-117.
Berzigotti et al., "Imaging in clinical decision-making for portal vein thrombosis" *Nat Rev Gastroenterol Hepatol.* (2014) 11(5):308-316.
Biecker E., (2013) "Portal hypertension and gastrointestinal bleeding: diagnosis, prevention and management" *World J Gastroenterol.* 19(31):5035-5050.
Blasco et al., "Hepatic venous pressure gradient identifies patents at risk of severe hepatitis C recurrence after liver transplantation" *Hepatology* 43:492-499 (2006).
Bloom et al., (2014) "Portal Hypertension—Pathophysiology, Diagnosis and Management" *Intern Med J.* [Epub ahead of print].
Bosch, J. et al. (2009) "The Clinical Use of HVPG Measurements in Chronic Liver Disease" *Nat. Rev. Gastroenterol. Hepatol.* 6(10):573-582.
Boyer et a;., "American Association for the Study of Liver Diseases The role of transjugular intrahepatic portosystemic shunt (TIPS) in the management of portal hypertension: Update 2009" *Hepatology* (2010) 51(1):306.
Boyvat et al., (2008) "Percutaneous sonographic guidance for TIPS in Budd-Chiari syndrome: direct simultaneous puncture of portal vein and inferior vena cava" *AJR Am J Roentgenol* 191:560-564.
Braga et al., "Modern hepatic imaging" *Surg Clin North Am.* (2004) 84(2):375-400.
Bruix et al., "Surgical resection of hepatocellular carcinoma in cirrhotic patients: prognostic value of preoperative portal pressure" *Gastroenterology* 111: 1018-1022 (1996).
Burroughs et al., "Assessment of therapeutic benefit of antiviral therapy in chronic hepatitis C: is hepatic venous pressure gradient a better end point?" *Gut* 50:425-421 (2002).
Carrion et al., "Efficacy of antiviral therapy on hepatitis C recurrence after liver transplantation: a randomized controlled study" *Gastroenterology* 132: 1746-1756 (2007).
Carrion et al., "Transient elastography for diagnosis of advanced fibrosis and portal hypertension in patient with hepatic C recurrence after liver transplantation" *Liver Transpl.* 12:1791-1798 (2006).
Chan et al., "Incidence, prognosis, and etiology of end-stage liver disease in patients receiving home total parenteral nutrition" *Surgery* (1999) 126(I):28-34.
Chatterjee, K. (2009) "The Swan-Ganz Catheters: Past, Present, and Future: A Viewpoint" *Circulation* 119(1): 147-152.
Cohen et al., "Hepatic imaging in the 21st century" *Semin Liver Dis.* (2006) 26(4):363-372.
Corso et al., (2008) "Treatment of Budd-Chiari syndrome with transjugular intrahepatic portosystemic shunt (TIPS)" *Radiol Med* 113:727-738.
Curi et al., "Molecular mechanisms of glutamine action" *J Cell Physiol.* (2005) 204(2):392-401.
De Franchis, R., "Evolving consensus in portal hypertension: report of the Baveno IV consensus workshop on methodology of diagnosis and therapy in portal hypertension" *J. Hepatol.* 43:167-176 (2005).
Diamanti et al., "Prevalence of liver complications in pediatric patients on home parenteral nutrition: indications for intestinal or combined liver-intestinal transplantation" *Transplant Proc.* (2003) 35(8):3047-3049.
Forner et al., "East meets the West—portal pressure predicts outcome of surgical resection for hepatocellular carcinoma" *Nat. Clin. Pract. Gastrenterol. Hepatol.* 6: 14-15 (2009).
Fuchs et al., "Stressing out over survival: glutamine as an apoptotic modulator" *J Surg Res.* (2006) 131(1):26-40.
Garcia-Tsao et al., "Management of varices and variceal hemorrhage in cirrhosis" *N Engl J Med.* (2010) 362(9):823-832.
Garcia-Tsao et al., Portal hypertension and variceal bleeding—unresolved issues: summary of an American Association for the Study of Liver Diseases and European Association for the Study of Liver Diseases and European Association for the Study of the Liver single-topic conference *Hepatology* 47:1764-1772 (2008).
Gasparini et al., (2002) "Transjugular intrahepatic portosystemic shunt by direct transcaval approach in patients with acute and hyperacute Budd-Chiari syndrome" *Eur J Gastroenterol Hepatol* 14:567-571.
Gasthuys, F. et al. (2009) "Transsplenic Portal Catheterization Combined with a Jugular Double-Lumen Catheter for Pharmacokinetic and Presystemic Metabolization Studies in Pigs" *J. Vet. Pharmacol. Ther.* 32(2):137-145.
Gazzera et al., (2009) "Fifteen years' experience with transjugular intrahepatic portosystemic shunt (TIPS) using bare stents: retrospective review of clinical and technical aspects" *Radiol Med* 114:83-94.
Gazzera, C. et al. (2013) "Ultrasound-Guided Transhepatic Puncture of the Hepatic Veins for TIPS Placement" *La Radiologia Medica* 118(3):379-385.
Geerts et al., "Prevention of venous thromboembolism: the Seventh ACCP Conference on Antithrombotic and Thrombolytic Therapy" *Chest* (2004) 126(3 Suppl):338S-400S.
Gluud et al., "Prognositic indicators in alcoholic cirrhotic men" *Hepatology* 8:222-227 (1988).
Haskal et al. (2003) "Quality improvement guidelines for transjugular intrahepatic portosystemic shunts" *J Vasc Interv Radiol* 14:S265-S270.
Heyland et al., "Total parenteral nutrition in the critically ill patient: a meta-analysis" *JAMA* (1998) 280(23): 2013-2019.
Ishizuka et al., "Total parenteral nutrition is a major risk factor for central venous catheter-related bloodstream infection in colorectal cancer patients receiving postoperative chemotherapy" *Eur Surg Res.* (2008) 41(4): 341-345.

(56) References Cited

OTHER PUBLICATIONS

Kalambokis et al., "Clinical outcome of HCV-related graft cirrhosis and prognostic value of hepatic venous pressure gradient" *Transpl, Int.* 22: 172-181 (2009).
Keller et al., "Effects of medium- and long-chain fatty acids on whole body leucine and glucose kinetics in man" *Metabolism* (2002) 51(6):754-760.
Kelly, D.A., "Liver complications of pediatric parenteral nutrition—epidemiology" *Nutrition* (1998) 14(1):153-157.
Kim et al., "Association of hyperglycemia and markers of hepatic dysfunction with dextrose infusion rates in Korean patients receiving total parenteral nutrition" *Am J Health Syst Pharm* (2003) 60(17):1760-1766.
Kumaret al., "Hepatic venous pressure gradient as a predictor of fibrosis in chronic liver disease because of hepatitis B virus" *Liver Int.* 28:690-698 (2008).
Lavoinne et al., "Glutamine and regulation of gene expression in rat hepatocytes: the role of cell swelling" *Biochimie* (1998) 80(10):807-811.
Lebrec et al., "Portal hypertension, size of esophageal varicies, and risk of gastrointestinal bleeding in alcoholic cirrohosis" *Gastroenterology* 79:1139-1144 (1980).
Lee et al., "Radiotherapeutic options for hepatocellular carcinoma with portal vein tumor thrombosis" *Liver Cancer* (2014) 3(1):18-30.
Lee, T. et al. (2005) "Tunneled Catheters in Hemodialysis Patients: Reasons and Subsequent Outcomes" *Am. J. Kidney Dis.* 46(3):501-508.
Lees et al., (2004) "Principles of pharmacodynamics and their applications in veterinary pharmacology" *J. Vet. Pharmacol. Ther.* 27(6):397-414.
Li et al., (2009) "Feasibility and midterm outcomes of percutaneous transhepatic balloon angioplasty for symptomatic Budd-Chiari syndrome secondary to hepatic venous obstruction" *J Vasc Surg* 50:1079-1084.
Liovet et al., "Intention-to-treat analysis of surgical treatment for early hepatocellular carcinoma: resectin versus transplantation" *Hepatology* 30:1434-1440 (1999).
Longo et al., (1992) "Color Doppler—US guidance in transjugular placement of intrahepatic portosystemic shunts" *Radiology* 184:281-284.
Lynch et al., "Potential role of leucine metabolism in the leucine-signaling pathway involving mTOR" *Am J Physiol Endocrinol Metab* (2003) 285(4):E854-863.
Marc Rhoads et al., "Glutamine, arginine, and leucine signaling in the intestine" *Amino Acids* (2009) 37(1):111-122.
Mates et al., "Pathways from glutamine to apoptosis" *Front Biosci.* (2006) 11:3164-3180.
Merkel et al., "Prognostic usefulness of hepatic vein catheterization in patients with cirrhosis and esophageal varices" *Gastroenterology* 102: 973-979 (1992).
Moore et al., "Early enteral feeding, compared with parenteral, reduces postoperative septic complications. The results of a meta-analysis" *Ann Surg.* (1992) 216(2):172-83.
Mordier et al., "Leucine limitation induces autophagy and activation of lysosome-dependent proteolysis in C2C12 myotubes through a mammalian target of rapamycin-independent signaling pathway" *J Biol Chem.* (2000) 275(38):29900-29906.
Nishimura et al., "Soybean oil in total parenteral nutrition maintains albumin and antioxidant enzyme mRNA levels" *Biol Pharm Bull.* (2005) 28(7):1265-1269.

Olson et al., "Transrenal-vein reflux ethanol sclerosis of gastroesophageal varices" *AJR Am J Roentgenol.* (1984) 143(3):627-628.
Ozaki et al., (2010) "Selective atrophy of the middle hepatic venous drainage area in hepatitis C-related cirrhotic liver: morphometric study by using multidetector CT" *Radiology* 257:705-714.
Petersen et al., (2001) "Intravascular US-guided direct intrahepatic portocaval shunt with a PTFE-covered stent-graft: feasibility study in swine and initial clinical results" *J Vasc Interv Radiol* 12:475-486.
Peynircioglu et al., (2010) "Is there an alternative to TIPS? Ultrasound-guided direct intrahepatic portosystemic shunt placement in Budd-Chiari syndrome" *Saudi J Gastroenterol* 16:315-318.
Pivonello et al., (2014) "The GH-IGF-SST system in hepatocellular carcinoma: biological and molecular pathogenetic mechanisms and therapeutic targets" *Infect Agent Cancer* 20:9-27.
Quateen et al., (2006) "Percutaneous transjugular direct portocaval shunt in patients with Budd-Chiari syndrome" *Cardiovasc Intervent Radiol* 29:565-570.
Raza et al., (2006) "Transhepatic puncture of portal and hepatic veins for TIPS using a single-needle pass under sonographic guidance" *AJR Am J Roentgenol* 187:W87-W91.
Rincon el al., "Prognostic value of hepatic venous pressure gradient for in-hospital mortality of patients with severe acute alcoholic hepatitis" *Aliment. Pharmacol. Ther.* 25:841-848 (2007).
Roberts et al., "Effect of sustained viral response on hepatic venous pressure gradient in hepatitis c-related cirrhosis" *Clin. Gastroenterol. Hepatol.* 5:932-937 (2001).
Ros et al., (2002) "Hepatic imaging. An overview" *Clin Liver Dis.* 6(1):1-16.
Samonakis et al., "Hepatic venous pressure gradient to assess fibrosis and its progression after liver transplantation for HCV cirrhosis" *Liver Transpl.* 13: 1305-1311 (2007).
Sen et al., "Albumin dialysis reduces portal pressure acutely in patients with severe alcoholic hepatitis" *J. Hepatol.* 43:142-148 (2005).
Sharma et al., (2004) "Pharmacological thrombolysis in Budd Chiari syndrome: a single centre experience and review of the literature" *J Hepatol* 40:172-180.
Sinagra et al., (2014) "Systematic review with meta-analysis: the haemodynamic effects of carvedilol compared with propranolol for portal hypertension in cirrhosis" *Aliment Pharmacol Ther.* 39(6):557-568.
Svoboda et al., "L-Glutamine-induced apoptosis in microglia is mediated by mitochondrial dysfunction" *Eur J Neurosci.* (2009) 30(2):196-206.
Tublin et al., (2008) "Altered liver morphology after portal vein thrombosis: not always cirrhosis" *Dig Dis Sci* 53:2784-2788.
Vorobioff et al., "Prevention of portal hypertension: From variceal development to clinical decompensation" *Hepatology* (2014) [Epub ahead of print].
Vorobioff et al., "Prognostic value of hepatic venous pressure gradient measurements in alchology cirrhosis: a 10-year prospective study" *Gastroenterology* 111: 701-709 (1996).
Wael et al., "Variations of Balloon-occluded Retrograde Transvenous Obliteration (BRTO): Balloon-occluded Antegrade Transvenous Obliteration (BATO) and Alternative/Adjunctive Routes for BRTO" *Semin Intervent Radiol.* (2011) 28(3):314-324.
Winters, R.W., "Total parenteral nutrition in pediatrics: the Borden award address" *Pediatrics* (1975) 56(1): 17-23.
Zaloga et al., "Total parenteral nutrition increases mortality after hemorrhage" *Crit Care Med* (1991) 19(1):54-59.

\* cited by examiner

VENOUS ACCESS CATHETERS AND METHODS FOR PORTAL VENOUS SYSTEM CATHETERIZATION

STATEMENT OF GOVERNMENT INTEREST

N.A.

FIELD OF THE INVENTION

The present invention contemplates devices and methods to administer nutritional compositions and/or therapeutic drugs directly into a portal venous system. For example, total parenteral nutrition therapy may be administered directly into the hepatic portal venous system thus circumventing known side effects of conventional parenteral administration. Alternatively, hepatic diseases and disorders may be treated using locally administered therapeutic drugs. Devices capable of direct portal venous system administration include, but are not limited to, a direct portal access catheter or a transjugular access catheter.

BACKGROUND

Hemorrhage from portosystemic varices remains a major cause of morbidity and mortality in patients with portal hypertension. Garcia-Tsao et al., "Management of varices and variceal hemorrhage in cirrhosis" *N Engl J Med.* (2010) 362(9):823-832. Shunting procedures, whether surgical or endovascular, are effective at reducing the portal pressure, but may result in serious complications such as encephalopathy and/or hepatic insufficiency. Boyer et al., "American Association for the Study of Liver Diseases The role of transjugular intrahepatic portosystemic shunt (TIPS) in the management of portal hypertension: Update 2009" *Hepatology* (2010) 51(1):306. These varices were usually accessed via the portal system, either by transhepatic, transileocolic vein, transumbilical vein, or transjugular vein route, and the sclerosant was introduced via the feeding vessels anterogradely. Recurrence rates were also high, likely due to recanalization through untreated collateral channels. With the introduction of balloon-occluded retrograde transvenous obliteration (BRTO) in the 1980s, there are now additional options of forcing sclerosant into the varices via the exit retrogradely, while occluding the outflow with a balloon. Olson et al., "Transrenal-vein reflux ethanol sclerosis of gastroesophageal varices" *AJR Am J Roentgenol.* (1984) 143(3):627-628. Because many variceal systems have multiple feeding and multiple draining pathways, combinations of anterograde and retrograde techniques are frequently useful. In addition, not all variceal systems drain into the left renal vein, and selection and occlusion of other outflow vessels may be necessary to eradicate varices effectively. Wael et al., "Variations of Balloon-occluded Retrograde Transvenous Obliteration (BRTO): Balloon-occluded Antegrade Transvenous Obliteration (BATO) and Alternative/Adjunctive Routes for BRTO" *Semin Intervent Radiol.* (2011) 28(3):314-324.

What is needed in the art are devices and methods to provide direct access catheterization of portal venous systems in an efficient and minimally invasive manner to provide therapy, assess tissue health and in the case of the hepatic portal system assess liver function and drug metabolism without interference from overall blood circulation pathways (i.e., the heart).

SUMMARY OF THE INVENTION

The present invention contemplates devices and methods to administer nutritional compositions and/or therapeutic drugs directly into a portal venous system. For example, total parenteral nutrition therapy may be administered directly into the hepatic portal venous system thus circumventing known side effects of conventional parenteral administration. Alternatively, hepatic diseases and disorders may be treated using locally administered therapeutic drugs. Devices capable of direct portal venous system administration include, but are not limited to, a direct portal access catheter or a transjugular portal access catheter.

In one embodiment, the present invention contemplates a transjugular portal access catheter device, comprising: a) a catheter body having a proximal end and a distal end and a tissue penetrator, wherein an anchor balloon is attached to said distal end; b) at least three lumens configured within said catheter body, wherein said first lumen extends between said proximal end and said distal end, said second lumen connects to said anchor balloon, and said third lumen extends from said proximal end and terminates before said distal end; and c) a connection hub interfaced with said three lumens, wherein said hub connects said three lumens to said proximal end of said catheter body. In one embodiment, the tissue penetrator is configured within said catheter body. In one embodiment, the catheter body further comprises an orientation apparatus attached to said catheter body. In one embodiment, the orientation apparatus comprises an imaging apparatus. In one embodiment, the third lumen terminates approximately 12 centimeters from said distal end of said catheter. In one embodiment, the connection hub further comprises a tunneled tissue ingrowth cuff.

In one embodiment, the present invention contemplates a direct portal access catheter device, comprising: a) a catheter body having a proximal end and a distal end and a tissue penetrator, wherein said distal end of said catheter contains an anchor balloon; b) at least two lumens configured within said catheter body, wherein said first lumen extends from said proximal end to said distal end, and said second lumen connects to said anchor balloon; and c) a connection hub interfaced with said first and second lumens and connects to said proximal end. In one embodiment, the tissue penetrator is configured within said catheter body. In one embodiment, the device further comprises an imaging apparatus attached to said catheter body. In one embodiment, the connection hub further comprises a tunneled tissue ingrowth cuff.

In one embodiment, the present invention contemplates a method, comprising; a) providing; i) a subject exhibiting at least one symptom of a disorder; ii) a portal access catheter comprising an anchor balloon; and iii) a composition capable of reducing said at least one symptom of said disorder; b) inserting said portal access catheter into a portal venous system; c) stabilizing said portal access catheter with said anchor balloon; and c) administering said composition with said portal access catheter into said portal venous system under conditions such that said at least one symptom of said disorder is reduced. In one embodiment, the portal access catheter is a transjugular portal access catheter. In one embodiment, the portal access catheter is a direct portal access catheter. In one embodiment, the transjugular portal access catheter is inserted via the jugular vein wherein the distal end of said catheter inserts into a hepatic portal vein and the distal end of said third lumen inserts into a cardiac right atrium. In one embodiment, the direct portal access catheter is a transabdominal catheter. In one embodiment, the transabdominal catheter is inserted via a percutaneous abdominal puncture. In one embodiment, the at least one symptom is selected from the group consisting of hepatic toxicity, a metabolic marker, hepatic cirrhosis, portal hypertension, elevated transaminase levels, viral titer, perisinusoidal fibrosis, elevated albumin levels, hepatocellular carcinoma size, gastroesophageal varices size. In one embodiment, the composition is selected from the group consisting of a total parenteral nutrition composition and a therapeutic compound composition. In one embodiment, the total parenteral nutrition composition comprises a plurality of amino acids, vitamins and folic acid. In one embodiment, the disorder comprises a portal hypertension disorder. In one embodiment, the therapeutic compound composition comprises a non-selective adrenergic beta-blocker. In one embodiment, the non-selective adrenergic beta-blocker is selected from the group consisting of propranolol and carvediol. In one embodiment, the therapeutic compound composition is selected from the group consisting of a vasopressor drug, an antibiotic and cyanoacrylate. In one embodiment, the vasopressor drug is terlipressin. In one embodiment, the disorder comprises a chronic viral hepatitis disorder. In one embodiment, the therapeutic compound composition is selected from the group consisting of peginterferon and antiviral drugs. In one embodiment, the disorder comprises an acute alcoholic hepatitis disorder. In one embodiment, the administering comprises a total parenteral nutrition composition. In one embodiment, the total parenteral nutrition composition comprises amino acids, vitamins and folic acid. In one embodiment, the disorder comprises a liver transplant. In one embodiment, the therapeutic compound composition comprises an immunosuppressive drug. In one embodiment, the disorder comprises a hepatocellular carcinoma disorder. In one embodiment, the therapeutic compound composition comprises a growth factor-RTK antibody. In one embodiment, the therapeutic compound composition comprises a growth factor-RTK receptor small molecule inhibitor. In one embodiment, the therapeutic composition comprises a cytoplasmic oncogenic kinase small molecule inhibitor. In one embodiment, the therapeutic compound composition comprises a synthetic somatostatin analogue. In one embodiment, the synthetic somatostatin analogue is selected from the group consisting of octreotide, lanreotide and pasireotide. In one embodiment, the disorder comprises a cirrhosis disorder. In one embodiment, the therapeutic compound composition is selected from the group consisting of a diuretic, vitamin K, a neurocognitive agent and an antibiotic. In one embodiment, the disorder comprises a hepatic thrombosis. In one embodiment, the therapeutic compound composition is selected from the group consisting of heparin, unfractionated heparin, low-molecular-weight heparin, aspirin, coumadin, warfarin, a vitamin K antagonist, and fondaparinux.

In one embodiment, the present invention contemplates a method, comprising; a) providing; i) a subject exhibiting at least one symptom of a disorder; ii) a portal access catheter comprising an endoscopic imaging device and an anchor balloon; and iii) a contrast agent; b) inserting said portal access catheter into a portal venous system; c) stabilizing said portal access catheter with said anchor balloon; d) administering said contrast agent with said portal access catheter into said portal venous system; and e) imaging said disorder with said endoscopic imaging device. In one embodiment, the portal access catheter is a transjugular portal access catheter. In one embodiment, the portal access catheter is a direct portal access catheter.

In one embodiment, the present invention contemplates a method, comprising: a) providing; i) a subject comprising a disorder; ii) a portal access catheter comprising an anchor balloon; and iii) a therapeutic compound capable of treating said disorder; b) inserting said portal access catheter into a portal venous system; c) stabilizing said portal access catheter with said anchor balloon; d) administering said therapeutic compound with said portal access catheter into said portal venous system at a first dose level under conditions such that a non-therapeutic level of said therapeutic compound is attained; and e) administering a second dose level of said therapeutic compound under conditions such that a therapeutic level of said therapeutic compound is attained. In one embodiment, the portal access catheter is a transjugular portal access catheter. In one embodiment, the portal access catheter is a direct portal access catheter. In one embodiment, the non-therapeutic level of said therapeutic compound is selected from the group consisting of a subtherapeutic level and a supratherapeutic level.

In one embodiment, the present invention contemplates a method, comprising; a) providing; i) a subject comprising a hepatic disorder; ii) a portal access catheter comprising an anchor balloon; and iii) a compound that undergoes hepatic first pass metabolism; b) inserting said portal access catheter into a portal venous system; c) stabilizing said portal access catheter with said anchor balloon; d) administering said compound with said portal access catheter into said portal venous system under conditions such that said compound undergoes hepatic first pass metabolism; and e) determining at least one metabolite level of said compound to assess the severity of said hepatic disorder. In one embodiment, the portal access catheter is a transjugular portal access catheter. In one embodiment, the portal access catheter is a direct portal access catheter. In one embodiment, the determining further comprises obtaining a hepatic vein blood sample with said portal access catheter.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" as used herein, in the context of any of any assay measurements refers to +/−5% of a given measurement.

The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing (e.g., autoantibody testing) to obtain further information on which to base a diagnosis.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disorder," "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides. The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that all trace impurities have been removed.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

DETAILED DESCRIPTION OF THE INVENTION

The present invention contemplates devices and methods to administer nutritional compositions and/or therapeutic drugs directly into a portal venous system. For example, total parenteral nutrition therapy may be administered directly into the hepatic portal venous system thus circumventing known side effects of conventional parenteral administration. Alternatively, hepatic diseases and disorders may be treated using locally administered therapeutic drugs. Devices capable of direct portal venous system administration include, but are not limited to, a direct portal access catheter or a transjugular access catheter.

I. The Portal Venous System

Figure 1:
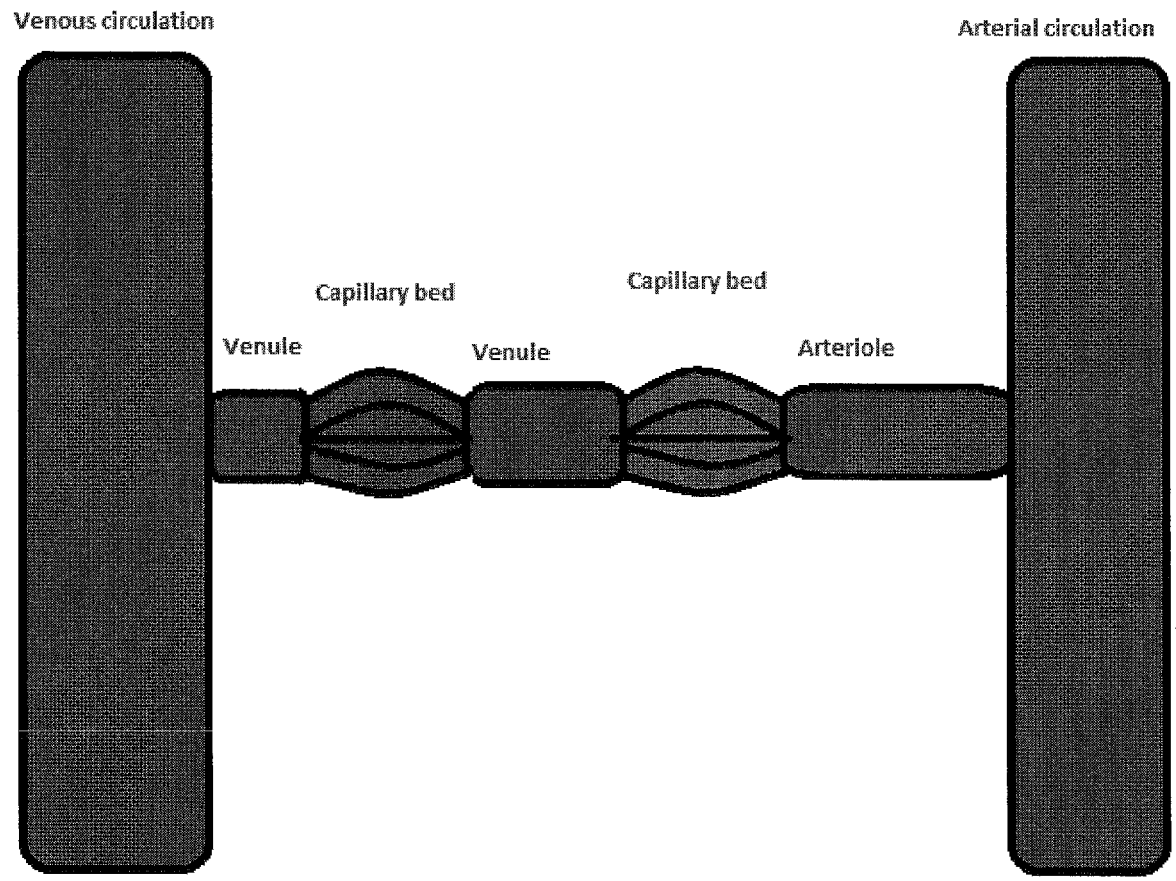
FIG. 1 illustrates a schematic representation of a portal venous system. A venous capillary bed is flanked by venules where the distal venule empties into an arterial capillary bed and subsequently into the arterial circulation system. As such, this represents a venous-arterial circulatory connection that bypasses the heart.
Figure 2:
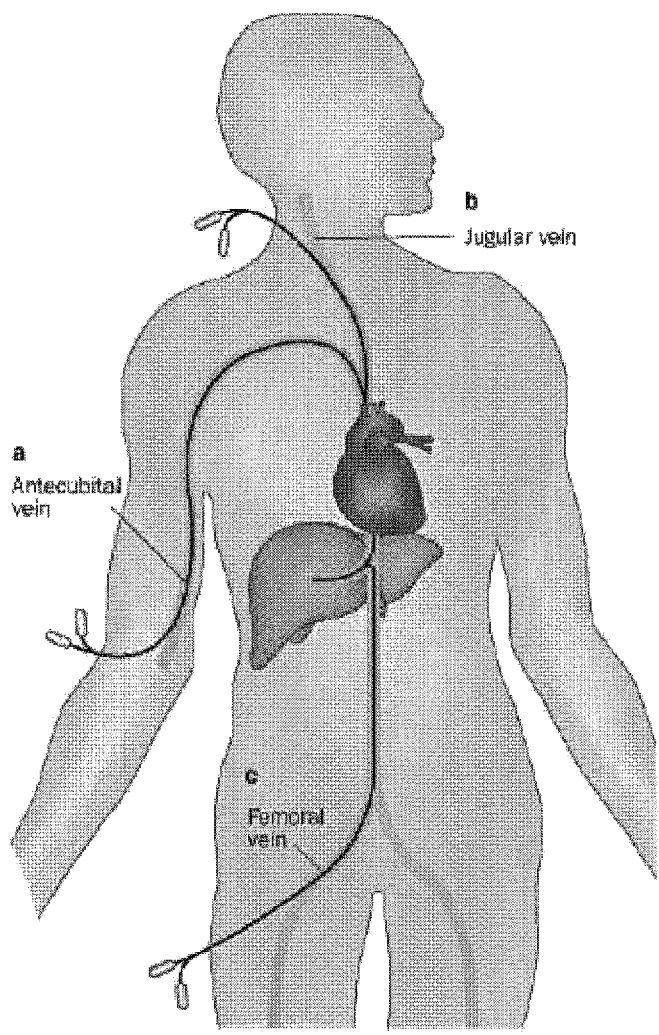
FIG. 2 illustrates a schematic representation of various venous access sites for hepatic vein catheterization: a. antecubital vein access; b. jugular vein access, or c. femoral vein access. As shown, the degree of invasiveness depends on the elected access site. Access via the antecubital vein is the least invasive approach and can be carried out on an outpatient basis. Access via the jugular or femoral veins is moderately invasive and usually is done in a hospital setting. The transjugular approach is the one most frequently used, as it enables a transvenous liver biopsy to be obtained as part of the procedure.

In the circulatory system of animals, a portal venous system occurs when a capillary bed pools into another capillary bed through veins, without first going through the heart. Both capillary beds and the blood vessels that connect them are considered part of the portal venous system. See, FIG. 1. Portal venous systems are relatively uncommon as a majority of capillary beds drain into veins which then drain directly into the heart, not into another capillary bed. Portal venous systems are considered venous because the blood vessels that join the two capillary beds are either veins or venules. Examples of portal venous systems include, but are not limited to, the hepatic portal system, the hypophyseal portal system and the renal portal system. The functional significance of portal venous systems are that they are capable of transporting relatively high concentrations of products from a first anatomical region directly to a second anatomical region. This has evolutionary significance, in that if the heart was integrated between those two anatomical regions, the high concentration of products would be circulated throughout the body.

In humans, one final common pathway for transport of venous blood from spleen, pancreas, gallbladder and an abdominal portion of a gastrointestinal tract (with the exception of the inferior part of the anal canal) is through the hepatic portal vein. It is believed that the hepatic portal vein may be formed by a union of superior mesenteric vein and splenic vein posterior to the pancreatic neck at the level of vertebra body L1. Ascending towards the liver, the portal vein passes posterior to the superior part of the duodenum and enters the right margin of the lesser omentum. As such, the hepatic portal vein is anterior to the omental foramen and posterior to both the bile duct, which is slightly to the right, and the hepatic artery proper, which is slightly to the left. On approaching the liver, the hepatic portal vein divides into right and left branches which enter the liver parenchyma and form several tributaries including, but not limited to; i) the right and left gastric veins, ii) the cystic vein and iii) the para-umbilical veins.

Transjugular intrahepatic portal systemic shunt (TIPS) has become a standard procedure for treating complications of portal hypertension refractory to medical and endoscopic therapy. Progressive advances in angiographic materials, increased operator experience and the use of ultrasound (US) routinely guide the portal puncture. Haskal et al. (2003) "Quality improvement guidelines for transjugular intrahepatic portosystemic shunts" *J Vasc Interv Radiol* 14:S265-S270; Longo et al., (1992) "Color Doppler-US guidance in transjugular placement of intrahepatic portosystemic shunts" *Radiology* 184:281-284; and Grosso et al., (1992) "Percutaneous transjugular intrahepatic portosystemic shunt (TIPS). The preliminary experience and proposal of a new method" *Radiol Med* 84:619-625. The hepatic veins amenable to TIPS are the right and the middle hepatic vein. These veins are usually catheterized via a retrograde transjugular approach from the inferior vena cava (IVC) to approach, by appropriately rotating the curved needle, the main intrahepatic portal branches 2-3 cm from the confluence. Identification of the most suitable hepatic vein for TIPS placement reduces the incidence of periprocedural complications and ensures optimal stent patency. However, in the rare cases in which the hepatic veins cannot be catheterized via a retrograde approach (because of recent and incomplete hepatic vein thrombosis, unilateral intrahepatic portal thrombosis, medial dislocation of the right main portal branch due to severe parenchymal atrophy, extrinsic compression of the IVC by the caudate lobe, expansile lesions at the hepatic vein confluence, etc.), ancillary techniques may be needed to successfully complete the procedure. Raza et al., (2006) "Transhepatic puncture of portal and hepatic veins for TIPS using a single-needle pass under sonographic guidance" *AJR Am J Roentgenol* 187:W87-W91; Gasparini et al., (2002) "Transjugular intrahepatic portosystemic shunt by direct transcaval approach in patients with acute and hyperacute Budd-Chiari syndrome" *Eur J Gastroenterol Hepatol* 14:567-571; Boyvat et al., (2008) "Percutaneous sonographic guidance for TIPS in Budd-Chiari syndrome: direct simultaneous puncture of portal vein and inferior vena cava" *AJR Am J Roentgenol* 191:560-564.

The conventional TIPS procedure, especially when carried out by expert operators and under US guidance, is successfully completed in almost all cases, and the shunt can be placed in either the right hepatic vein (more easy to catheterize via retrograde approach under fluoroscopic guidance) or the middle hepatic vein. Gazzera et al., (2009) "Fifteen years' experience with transjugular intrahepatic portosystemic shunt (TIPS) using bare stents: retrospective review of clinical and technical aspects" *Radiol Med* 114: 83-94. However, in certain conditions (5% of cases)—such as complete thrombosis of a portal hemisystem, severe hypotrophy of liver segments V and VIII (which alters anatomical relationships between the right portal branches and the ipsilateral hepatic vein) and incomplete Budd-Chiari syndromes—only one hepatic vein will be suitable for shunting, but its transostial catheterization may prove impossible. Tublin et al., (2008) "Altered liver morphology after portal vein thrombosis: not always cirrhosis" *Dig Dis Sci* 53:2784-2788; Yoshiura et al., (1998) "Extreme right lobar atrophy of the liver: a rare complication of autoimmune hepatitis" *J Clin Gastroenterol* 26:334-336; Ozaki et al., (2010) "Selective atrophy of the middle hepatic venous drainage area in hepatitis C-related cirrhotic liver: morphometric study by using multidetector CT" *Radiology* 257: 705-714; Rhu et al., (2005) "Management of Budd-Chiari syndrome" *Dig Dis Sci* 50:540-546; Shainia et al., (2004) "Pharmacological thrombolysis in Budd Chiari syndrome: a single centre experience and review of the literature" *J Hepatol* 40:172-180; Li et al., (2009) "Feasibility and midterm outcomes of percutaneous transhepatic balloon angioplasty for symptomatic Budd-Chiari syndrome secondary to hepatic venous obstruction" *J Vasc Surg* 50:1079-1084; Corso et al., (2008) "Treatment of Budd-Chiari syndrome with transjugular intrahepatic portosystemic shunt (TIPS)" *Radiol Med* 113:727-738. In these cases, US-guided percutaneous puncture of the target hepatic vein allows resolution of one of the earliest technical problems that may arise during TIPS placement, where the procedure may be completed in only a few minutes and with a minimal amount of additional angiographic material. One other contraindication for percutaneous puncture of a hepatic vein is complete Budd-Chiari syndrome, in which case TIPS can only be performed through direct portal puncture from the IVC or through direct intrahepatic portosystemic shunt (DIPS), a technique that involves the simultaneous percutaneous puncture of the intrahepatic portal vein and retrohepatic IVC under US guidance. Quateen et al., (2006) "Percutaneous transjugular direct portocaval shunt in patients with Budd-Chiari syndrome" *Cardiovasc Intervent Radiol* 29:565-570; Yang et al., (1997) "Reestablishment of second hepatic hilum: a new technique for treatment of Budd-Chiari syndrome" *Radiol Pract* 12:47-51; Petersen et al., (2001) "Intravascular US-guided direct intrahepatic portocaval shunt with a PTFE-covered stent-graft: feasibility study in swine and initial clinical results" *J Vasc Interv Radiol* 12:475-486; and Peynircioglu et al., (2010) "Is there an alternative to TIPS? Ultrasound-guided direct intrahepatic portosystemic shunt placement in Budd-Chiari syndrome" *Saudi J Gastroenterol* 16:315-318.

II. Conventional Catheters

Pulmonary artery catheterization (PAC) has been suggested as a tool to perform hemodynamic monitoring in critically ill patients. For example, a standard pulmonary artery catheter usually have two lumens (e.g., for example, a Swan-Ganz catheter). Swan-Ganz catheters usually have an inflatable balloon at the tip which primarily facilitates catheter placement into a pulmonary artery. However, the Swan-Ganz balloon, when inflated, also may be used to provide an indirect measurement of left atrial blood pressure. Conventional PAC catheters may have multiple lumens having a series of openings along the length to allow administration of various compounds. PAC's commonly have lumens with: i) a distal temperature thermistor; ii) a proximal port for CVP monitoring, and fluid/drug administration; iii) a distal port for PAP monitoring; iv) a variable infusion port (VIP) for fluid and drug administration; and v) an inflatable balloon for blood pressure measurement. PAC's are not designed for permanent placement, but are temporary to provide short-term measurements and administration to a patient. Chatterjee, K. (2009) "The Swan-Ganz Catheters: Past, Present, and Future: A Viewpoint" *Circulation* 119(1): 147-152. It is noted that Swanz-Ganz catheters do not teach a multi-lumen transjugular catheter device with a tissue penetrator and anchoring balloon, nor have Swanz-Ganz catheters been reported to be used in methods of monitoring a direct liver drug response and/or direct hepatic delivery of therapeutic agents.

A retrospective analysis of transjugular intrahepatic portal systemic shunt (TIPS) performed with ultrasound (US)-guided percutaneous puncture of the hepatic veins reported that the best success rates were observed in conjunction with a percutaneous puncture. Gazzera, C. et al. (2013) "Ultrasound-Guided Transhepatic Puncture of the Hepatic Veins for TIPS Placement" *La Radiologia Medica* 118(3):379-385. However, these TIPS methods were not performed with an improved catheter configured with at least two lumens and a distal end anchor balloon, nor does it describe the methods of monitoring direct liver drug response or direct hepatic delivery of therapeutic agents.

Measurement of the hepatic venous pressure gradient (HVPG) using a transjugular catheterization to evaluate the presence and severity of portal hypertension has been reported. Bosch, J. et al. (2009) "The Clinical Use of HVPG Measurements in Chronic Liver Disease" *Nat. Rev. Gastroenterol. Hepatol.* 6(10):573-582. HVPG was measured by hepatic vein catheterization and required a simultaneous puncture of a hepatic vein and a portal vein. The portal pressure gradient (measured as HVPG) is the difference between the wedged hepatic venous pressure (WHVP) and the free hepatic venous pressure (FHVP). The WHVP is measured by occluding the hepatic vein with an inflatable balloon, thereby stopping the blood flow and causing a static column of blood that equalizes the pressure with the preceding vascular territory. However, the reference does not teach a specific type of multi-lumen transjugular catheter device, nor does it describe the methods of monitoring direct liver drug response or direct hepatic delivery of therapeutic agents.

The surgical placement of a portal catheter system was reported for monitoring liver drug response (pharmacokinetics and also the first-pass effect of drugs) in pigs. Gasthuys, F. et al. (2009) "Transsplenic Portal Catheterization Combined with a Jugular Double-Lumen Catheter for Pharmacokinetic and Presystemic Metabolization Studies in Pigs" *J. Vet. Pharmacol. Ther.* 32(2):137-145. However, the reference does not teach a specific type of multi-lumen transjugular catheter device, nor does it describe the methods of monitoring direct liver drug response or direct hepatic delivery of therapeutic agents.

Tunneled catheters have been used in hemodialysis patients to assess the risks of catheter-related complications, such as bacteremia. Lee, T. et al. (2005) "Tunneled Catheters in Hemodialysis Patients: Reasons and Subsequent Outcomes" *Am. J. Kidney Dis.* 46(3):501-508. Tunneled catheters that access the liver or the specific type of multi-lumen transjugular catheter device are not suggested, nor does the study provide methods of monitoring direct liver drug response or direct hepatic delivery of therapeutic agents.

The transjugular liver biopsy (TJLB) procedures have been reported consisting of obtaining liver tissue through a rigid cannula introduced into one of the hepatic veins, typically using jugular venous access often using ultrasound assistance for positioning. Typically this procedure is not meant to have a permanent access to the liver, nor does it include a transportal access. Tab 7. Behrens et al. (2012) "Transjugular Liver Biopsy" *Semin. Intervent. Radial.* 29(2):111-117. As such, the reference does not teach a specific type of multi-lumen transjugular catheter device, nor does it describe the methods of monitoring direct liver drug response or direct hepatic delivery of therapeutic agents.

An apparatus method for establishing a transjugular intrahepatic portosystemic shunt between the portal vein from a hepatic vein was reported where the apparatus comprises an elongated hollow outer guide; an outer handle having an inner lumen and a first luer lock, the outer handle attached at a proximal end of the outer guide, the outer guide in flow communication with the inner lumen and the first luer lock; an elongated hollow inner needle; and a hub having a second luer lock, the hub attached at a proximal end of the inner needle, the inner needle in flow communication with the second luer lock. The inner needle is slidingly received into the outer guide through the inner lumen. The inner needle rotates within the outer guide by manipulation of the hub; and a distal tip of the inner needle is deployed out of and beyond a distal tip of the outer guide. Kahn et al., "Transjugular Intrahepatic Portosystemic Shunt Device," U.S. Pat. No. 8,628,491 (herein incorporated by reference). However, the reference does not teach any specific type of multi-lumen transjugular catheter device, nor does it describe methods of monitoring direct liver drug response or direct hepatic delivery of therapeutic agents.

A device designed to improve the safety and efficacy of catheterization of the portal vein during a TIPS procedure and an associated method, simultaneously advanced multiple sequentially smaller needles through a liver parenchyma from the distal end of the TIPS needle. In so doing, the device allowed sampling from the liver with each pass and facilitated catheterization of the portal vein from the hepatic vein. Kahn et al. "Multi-Needle Transjugular Intrahepatic Portosystemic Shunt Device" U.S. Pat. No. 8,287,481 (herein incorporated by reference). However, the reference does not teach any specific type of multi-lumen transjugular catheter device, nor does it describe the methods of monitoring direct liver drug response or direct hepatic delivery of therapeutic agents.

A comparison of an open hub system and a closed hub system for catheters for pulmonary arterial hypertension patients in relation to catheter-related infections has been reported. Akagi et al., (2007) "Prevention of Catheter-Related Infections Using a Closed Hub System in Patients with Pulmonary Arterial Hypertension" *Circ. J.* 71(4):559-564. However, the reference does not teach any specific type of multi-lumen transjugular catheter device, nor does it describe the methods of monitoring direct liver drug response or direct hepatic delivery of therapeutic agents.

III. Portal Venous Access Catheters

Portal venous access catheters contemplated herein are an improvement over conventional catheters in that the presently disclosed transvenous approach allows a second lumen within the systemic venous circulation in addition to the portal lumen. The presently disclosed catheters differ from conventional catheters in design in that they comprise a distal anchor balloon providing advantages including, but not limited to: i) occlude the catheterized vessel; and ii) prevent respiratory motion-induced dislodgement (an unavoidable problem when using conventional catheters).

In one embodiment, the present invention contemplates a catheter configured to access to a portal venous system. In one embodiment, the portal venous system comprises the hepatic portal venous system. In one embodiment, an abdominal percutaneous insertion site provides access to the hepatic portal venous system. In one embodiment, the catheter is a temporary catheter. In one embodiment, the catheter is a long-term tunneled catheter. In one embodiment, an internal jugular insertion site provides access to the hepatic portal venous systems. In one embodiment, the internal jugular insertion site further comprises a hepatic vein.

In one embodiment, the present invention contemplates a method providing a portal venous system access catheter for administering nutritional supplements.

In one embodiment, the present invention contemplates a method providing a portal venous system access catheter for administering therapeutic compounds. In one embodiment, the therapeutic compound comprises an anti-cancer agent.

In one embodiment, the present invention contemplates a method providing a portal venous system access catheter for performing metabolism research.

Although it is not necessary to understand the mechanism of an invention, it is believed that conventional catheters are not designed for portal venous access. In particular, conventional venous infusion catheters are not configured with an anchoring balloon. In some embodiments, the present invention contemplates a tunneling catheter design that provides for a customized "sized fit" by tailoring each catheter to a different size. In one embodiment, the tissue retention sheath of the portal access catheter is separate from the catheter body. Consequently, the tissue retention sheath, in conjunction with the connection hub, can be inserted into a tailored catheter wherein the tissue retention cuff remains peripheral to the entry site. Such venous access catheters contemplated herein are constructed out of polymer materials currently available and used in conventional catheters. In other embodiments, the catheters are heparinized.

A. Direct Portal Venous Access Catheters

In some embodiments, the present invention contemplates methods using a direct portal venous access catheter for treatments including, but not limited to, parenteral nutrition, portal vein embolization to allow infusion of a hepatic contralateral lobe to increase growth of a future liver remnant (FLR), direct portal infusions for malignancy (i.e., for example, infusion hepatoprotective medicines while treating with chemotherapeutic compounds that is toxic to tumor), imaging research for direct assessment of hepatic metabolism (using special imaging compounds such as hyperpolarized C13), portal vein thrombolysis in cases of portal thrombosis, retained portal vein access in cases where a portal intervention is staged, i.e. transportal variceal embolization. In other embodiments, a central venous access catheter may be used to treat end-stage vasculopaths with dialysis or antibiotics.

Figure 3:
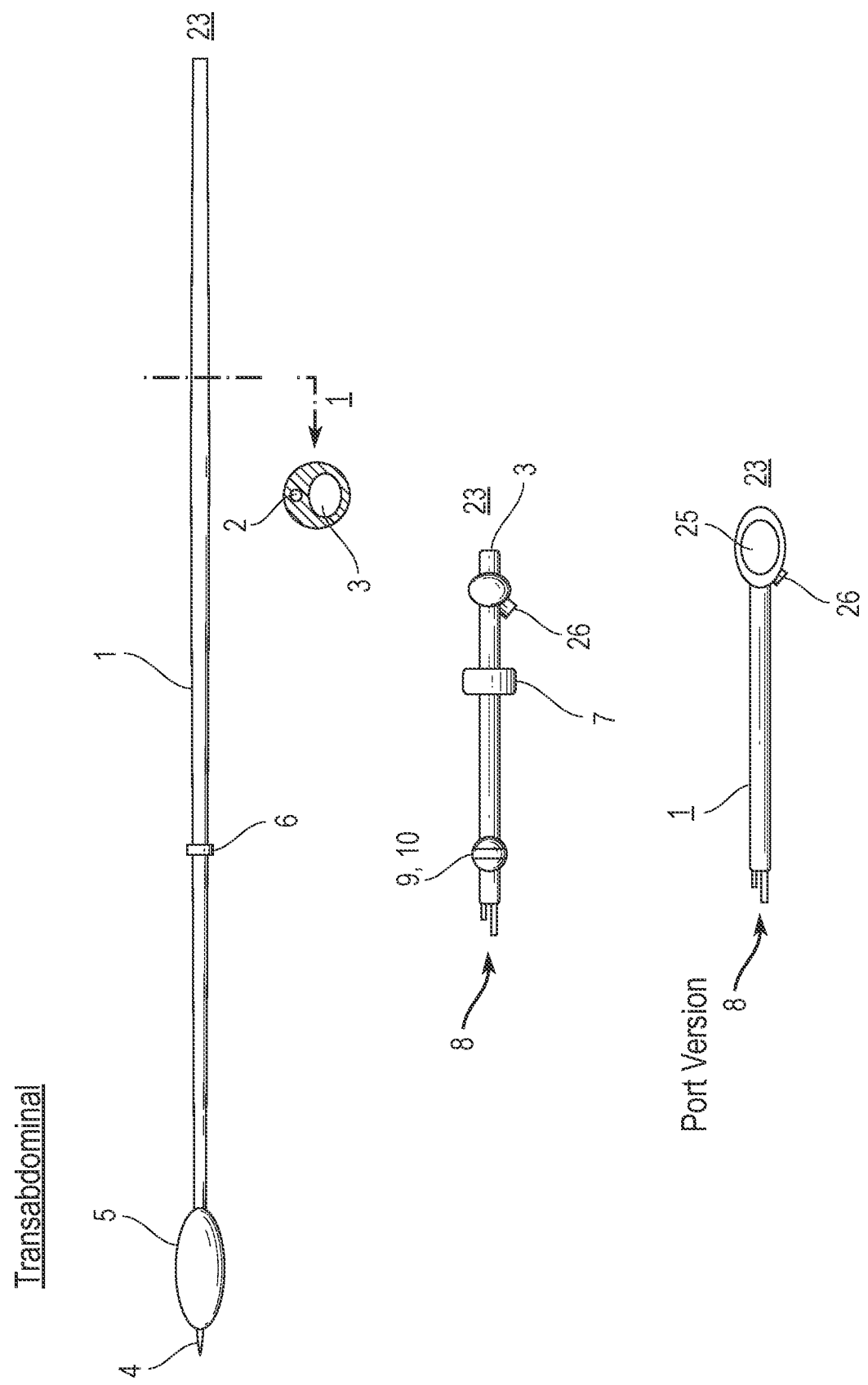
FIG. 3 illustrates one embodiment of a direct portal venous access catheter.

In particular reference to FIG. 3, a catheter body (1) is configured with a balloon-fill lumen (2) and a main lumen (3). Attached to the distal tip (4) of the catheter body (1) is an inflatable anchor balloon (5). A ring slide (6) or hemostatic clamp (7) surrounds the catheter body (1) and may be moved longitudinally to secure to a metal connector (8) protruding from the proximal end of the catheter body (1). A tunnel tissue ingrowth cuff (9) is attached to the proximal end of the catheter body (1) proximate to the metal connector (8). In other embodiments, the tunnel tissue ingrowth cuff (9) is replaced with suture slots (10). In a port version shown in FIG. 3, the proximal end (23) of the catheter body (1) has a subcutaneous port (25) connected to the main lumen (3) and a balloon-fill port (26) connected to the balloon-fill lumen (2). The balloon-fill port (26) is oriented perpendicular to the subcutaneous port (25).

B. Transjugular Portal Venous Access Catheters

In some embodiments, a transjugular catheter may be used for treatments including, but not limited to, total parenteral nutrition compositions without the need for multiple catheters in the setting of critical illness, drug development assays (e.g., for example, direct assessment of first pass metabolism and/or hepatotoxicity data) much more readily than current methods, drug pharmacokinetic metabolism and nutritional effects by giving drugs portally and then measuring concentrations post-portally. In one embodiment, the transjugular portal access catheter is attached to a liver assist/liver bypass-dialysis machine for artificial management of homeostasis.

In other embodiments, the transjugular portal venous access catheter may be used to determine changes in amino acid, fatty acid, and other metabolite concentrations as these compound pass through the liver.

Figure 4:
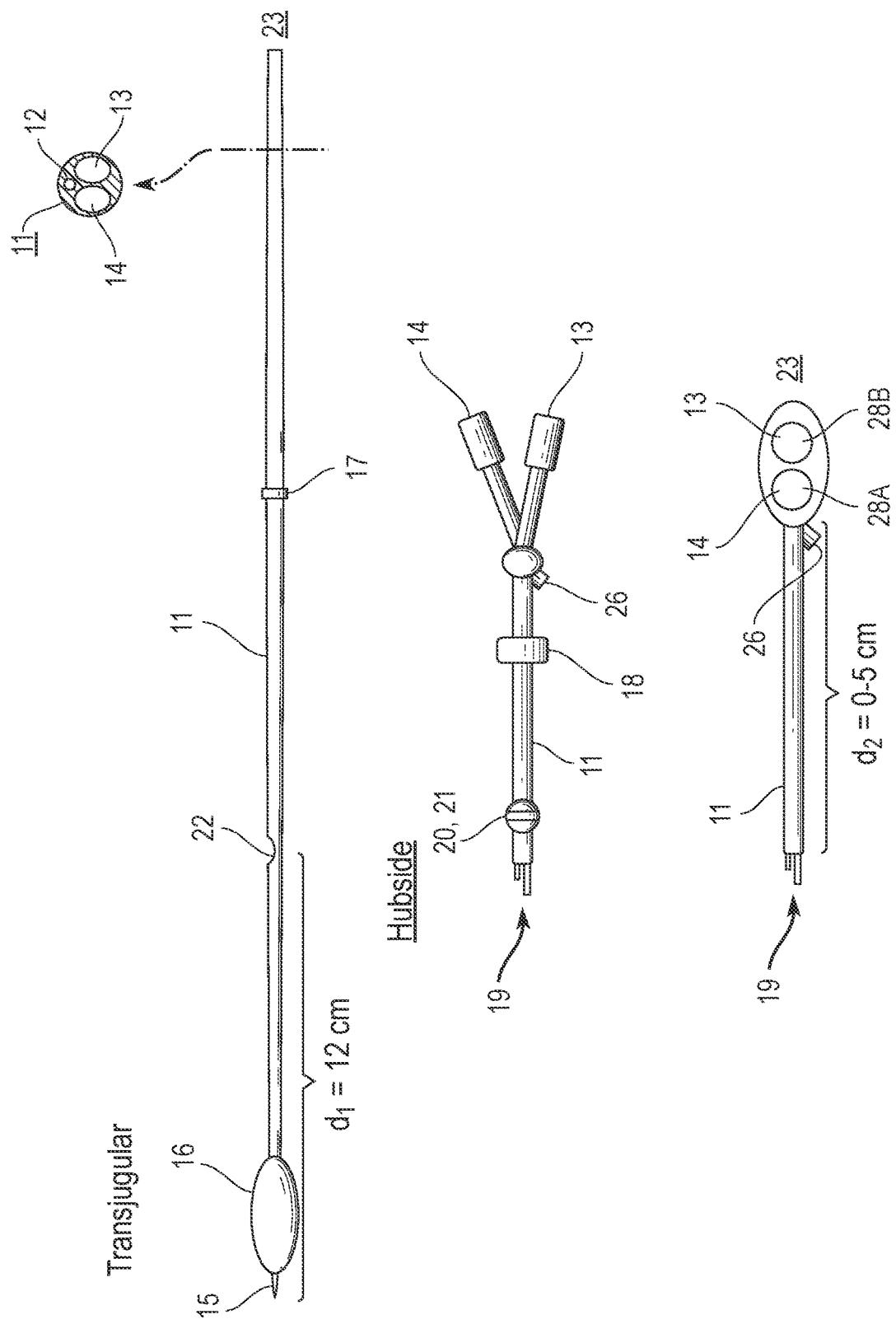
FIG. 4 illustrates one embodiment of a transjugular venous access catheter.

In particular reference to FIG. 4, a catheter body (11) is configured with a balloon-fill lumen (12) a portal venous lumen (13) and a central venous lumen (14). Attached to the distal tip (15) of the catheter body (11) is an inflatable anchor balloon (16). A ring slide (17) or hemostatic clamp (18) surrounds the catheter body (11) and may be moved longitudinally to secure to a metal connector (19) protruding from the proximal end of the catheter body (11). The catheter body (11) bifurcates to separate the portal venous lumen (13) from the central venous lumen (14) and the balloon-fill lumen (12). A tunnel tissue ingrowth cuff (20) is attached to the proximal end of the catheter body (11) proximate to the metal connector (19). In other embodiments, the tunnel tissue ingrowth cuff (20) is replaced with suture slots (21). A transjugular catheter is shown having the central venous lumen (14) terminate at a cutaneous end hole (22) a distance $d_1$, e.g., approximately 12 centimeters, from said distal end (15) of the catheter body (11). In a port version shown in FIG. 4, the proximal end (23) of the catheter body (11) has a subcutaneous port (28) with a first access port (28A) connected to the central venous lumen (14) and a second access port (28B) connected to the portal venous lumen (13) and a balloon-fill port (26) connected to the balloon-fill lumen (12). The balloon-fill port (26) is oriented perpendicular to the subcutaneous port (25). The metal connector (19) may be spaced a distance $d_2$ between 0 and 5 cm from the subcutaneous port (28).

VI. Total Parenteral Nutrition

Total parenteral nutrition (TPN) has been used in medicine since the early 1970's for patients that are unable to eat sufficiently to support metabolism. TPN is also used to maintain adequate nutrition in preparation for surgery. Fleming et al., "Total parenteral nutrition" *Mayo Clin Proc.* (1976) 51(3):187-199; and Winters, R. W., "Total parenteral nutrition in pediatrics: the Borden award address" *Pediatrics* (1975) 56(1): 17-23. In its present form, TPN may involve the delivery of nutrients and minerals via a catheter inserted into a large central vein (i.e., for example, the superior vena cava). However, there are certain disadvantages associated with current methods of TPN delivery including, but not limited to well-characterized metabolic complications. Specifically, central venous delivery of TPN is inconsistent with normal nutrient intake where, under normal physiologic conditions, nutrients enter the gastrointestinal (GI) tract and drain into vascular arcades that supply the small intestine. This provides an ability for all venous drainage from the bowels to pass through the liver where amino acid, lipid, and glucose concentrations are carefully modulated by periportal hepatocytes.

A further disadvantage of TPN is the development of toxicities including, but not limited to, cholestasis, hepatic dysfunction, and/or systemic infection. Forchielli et al., "Nutritional factors contributing to the development of cholestasis during total parenteral nutrition" *Adv Pediatr.* (2003) 50: 245-267; Ishizuka et al., "Total parenteral nutrition is a major risk factor for central venous catheter-related bloodstream infection in colorectal cancer patients receiving postoperative chemotherapy" *Eur Surg Res.* (2008) 41(4): 341-345; Kim et al., "Association of hyperglycemia and markers of hepatic dysfunction with dextrose infusion rates in Korean patients receiving total parenteral nutrition" *Am J Health Syst Pharm* (2003) 60(17):1760-1766; and Zaloga et al., "Total parenteral nutrition increases mortality after hemorrhage" *Crit Care Med* (1991) 19(1):54-59. In a severe form, these toxic TPN side effects can be seen in 40-60% of infants requiring long-term TPN for conditions including, but not limited to, short-gut syndrome and/or intestinal failure, and in 15% of adults administered with TPN in a non-clinical setting (i.e., for example, at home). Diamanti et al., "Prevalence of liver complications in pediatric patients on home parenteral nutrition: indications for intestinal or combined liver-intestinal transplantation" *Transplant Proc.* (2003) 35(8):3047-3049; Kelly, D. A., "Liver complications of pediatric parenteral nutrition—epidemiology" *Nutrition* (1998) 14(1):153-157; and Chan et al., "Incidence, prognosis, and etiology of end-stage liver disease in patients receiving home total parenteral nutrition" *Surgery* (1999) 126(1):28-34. In addition, there is little evidence that TPN in its current form is actually clinically helpful in medicine. McGeer et al., "Parenteral nutrition in cancer patients undergoing chemotherapy: a meta-analysis" *Nutrition* (1990) 6(3):233-2401; Moore et al., "Early enteral feeding, compared with parenteral, reduces postoperative septic complications. The results of a meta-analysis" *Ann Surg.* (1992) 216(2):172-83; and Heyland et al., "Total parenteral nutrition in the critically ill patient: a meta-analysis" *JAMA* (1998) 280(23): 2013-2019. Despite greater focus on customized formulations of TPN, these are reported to have produced only marginally improved outcomes, with TPN related morbidity remaining a significant clinical problem. Nishimura et al., "Soybean oil in total parenteral nutrition maintains albumin and antioxidant enzyme mRNA levels" *Biol Pharm Bull.* (2005) 28(7):1265-1269. The patient population at greatest risk of complications is TPN-dependent children with short-gut syndrome. If the toxic complications of parenteral nutrition were eliminated then it would be clinically useful in more situations.

In some embodiments, the present invention overcomes the disadvantages of TPN-related toxicity by contemplating methods for delivering the parenteral nutrition into the circulation in which substrate enters the body using physiologically normal pathways. For example, when food is taken enterally (e.g., eating via the mouth, throat, stomach and small intestine) the nutrients enter the body exclusively via the portal venous circulation. The portal venous circulatory route of nutrient absorption plays a role in maintaining the correct balance of substrate concentrations in serum (e.g., providing secondary signaling functions), as well as detoxification by the liver (i.e., for example, first pass metabolism). The liver is believed capable of functioning and maintaining appropriate systemic metabolic homeostasis over a wide variety of enteral intake, as well as regulating and balancing substrate availability. Although it is not necessary to understand the mechanism of an invention, it is believed that TPN administration into the portal venous system may allow the liver to properly regulate the levels of circulating amino acids and avoid the toxic side events when delivered via the central venous system.

While the mechanisms of TPN side effects of hepatic dysfunction and/or cholestasis have not yet been fully elucidated, these conditions may be related to secondary signaling functions of the amino acids both within the systemic circulation as well as the portal circulation. Amino acid imbalances are thought to occur primarily because first pass metabolism of nutrients, substrates, and toxins by the GI tract and liver cannot occur when TPN is delivered into a central vein.

V. Amino Acid Regulation

Many amino acids regulated by the liver have important signaling functions. Those with well-defined roles in signaling include, but are not limited to, leucine, glutamine, arginine and/or proline. For example, leucine is believed to be involved in growth regulation and insulin signaling; glutamine is believed to play a role in growth and wasting; arginine is believed to influence vasoconstriction; and proline is believed to play a role in P53 signaling and apoptosis. There several reports that suggest branched chain amino acids (BCAA), leucine specifically, activates mTOR in the growth and protein synthesis pathway and that an absence of leucine can actually trigger autophagy and proteolysis pathways. Anthony et al., "Leucine stimulates translation initiation in skeletal muscle of postabsorptive rats via a rapamycin-sensitive pathway" *J Nutr.* (2000) 130(10): 2413-2419; Lynch et al., "Potential role of leucine metabolism in the leucine-signaling pathway involving mTOR" *Am J Physiol Endocrinol Metab* (2003) 285(4):E854-863; Marc Rhoads et al., "Glutamine, arginine, and leucine signaling in the intestine" *Amino Acids* (2009) 37(1):111-122; Mordier et al., "Leucine limitation induces autophagy and activation of lysosome-dependent proteolysis in C2C12 myotubes through a mammalian target of rapamycin-independent signaling pathway" *J Biol Chem.* (2000) 275(38):29900-29906. As such, it is believed that circumventing the liver by delivering amino acids (e.g., for example, by TPN) centrally would be expected to deprive the liver of a significant signaling mechanism.

It has been observed that hepatocytes have well-developed amino acid uptake mechanisms and that a significant proportion of hepatocyte dry weight is devoted to amino acid metabolism (data not shown). For example, it has been reported that leucine levels are tightly regulated in response to levels of fatty acids in the blood and liver and that branched chain amino acid metabolism dysregulation has been implicated in wasting associated with liver disease. Cabre et al., "Nutritional issues in cirrhosis and liver transplantation" *Curr Opin Clin Nutr Metab Care* (1999) 2(5): 373-380; and Keller et al., "Effects of medium- and long-chain fatty acids on whole body leucine and glucose kinetics in man" *Metabolism* (2002) 51(6):754-760. Glutamine has been shown to participate in the regulation of apoptosis, mitochondrial growth, calcium buffering, insulin signaling, lipogenesis, DNA replication, osmotic stress, glutathione metabolism, as well as protein synthesis. Fuchs et al., "Stressing out over survival: glutamine as an apoptotic modulator" *J Surg Res.* (2006) 131(1):26-40; Lavoinne et al., "Glutamine and regulation of gene expression in rat hepatocytes: the role of cell swelling" *Biochimie* (1998) 80(10):807-811; Mates et al., "Pathways from glutamine to apoptosis" *Front Biosci.* (2006) 11:3164-3180; and Svoboda et al., "L-Glutamine-induced apoptosis in microglia is mediated by mitochondrial dysfunction" *Eur J Neurosci.* (2009) 30(2):196-206. It has also been reported that serum concentrations of glutamine are maintained in a fairly narrow range in animals, responding to nutrient intake and serum insulin levels. Curi et al., "Molecular mechanisms of glutamine action" *J Cell Physiol.* (2005) 204(2):392-401.

Although it is not necessary to understand the mechanism of an invention it is believed that direct portal venous system feeding (e.g., for example, TPN) can be successfully administered while maintaining amino acid homeostasis and hepatic first pass metabolism/detoxification. It is also believed that direct portal venous system feeding would minimize random and/or aberrant amino acid signaling in the liver resulting from peripheral amino acid catabolism. For example, peripheral tissues without an intact urea cycle usually have well-developed mechanisms of amino acid uptake, however, these uptake systems generally exclude arginine and alanine and are concomitantly released into the blood stream during amino acid catabolism. In contrast, peripheral tissues with an intact urea cycle (which are believed to completely metabolize amino acids) are able to dispose of the nitrogen group of amino acids. Consequently, the serum concentration of amino acids including, but not limited to, arginine and/or alanine, may act as starvation signals to hepatocytes.

In some embodiment, the present invention contemplates developing a catheter designed to accommodate hepatic movement using a different retention mechanism as compared to currently available catheters. Consequently, catheter embodiments described herein are designed to accommodate hepatic anatomy.

VI. Hepatic Disorders

A. Portal Hypertension

Portal hypertension is believed to be a complication of liver disease, although other conditions may also be implicated. As a result of elevated pressures within the portal vein a number of complications can arise including, but not limited to, the development of oesophageal and gastric varices, ascites, hepatic encephalopathy as well as complications secondary to circulatory dysfunction such as hepatorenal syndrome, portopulmonary syndrome and hepatopulmonary syndrome. Bloom et al., (2014) "Portal Hypertension—Pathophysiology, Diagnosis and Management" *Intern Med J.* [Epub ahead of print].

Pharmacological treatment of portal hypertension (PH) is usually directed to gastro-esophageal varices related events at different frameworks including prophylactic, emergency or preventive therapy. The goals of treatment are to avoid a first bleeding episode, stop active bleeding and prevent bleeding recurrence, respectively. The objective of pre-primary prophylaxis is to avoid variceal development and therefore, it necessarily deals with cirrhotic patients at earlier stages of the disease. At these earlier stages, non-selective beta blocker have been ineffective in preventing the development of varices and other complications of PH. Therefore, treatment should not rely on NSBB. It is possible, that at these earlier stages, etiological treatment of liver disease itself could prevent the progression of PH. Early treatment of PH, if successful, may translate into histological-hemodynamic improvements, avoiding not only variceal development but also other PH related complications, such as ascites and porto-systemic encephalopathy (PSE). Vorobioff et al., "Prevention of portal hypertension: From variceal development to clinical decompensation" *Hepatology* (2014) [Epub ahead of print].

In developed PH, however, adrenergic beta-blockers have been identified as the drug of choice. For example, propranolol is recommended for prophylaxis of variceal bleeding in cirrhosis. However, carvedilol is a non-selective beta-blocker with a mild anti-alpha-1-adrenergic activity and has been shown to be more effective than propranolol in reducing PH. Sinagra et al., (2014) "Systematic review with meta-analysis: the haemodynamic effects of carvedilol compared with propranolol for portal hypertension in cirrhosis" *Aliment Pharmacol Ther.* 39(6):557-568.

Bleeding from esophageal varices is a life threatening complication of portal hypertension. Primary prevention of bleeding in patients at risk for a first bleeding episode is therefore a major goal. Medical prophylaxis usually takes the place of non-selective beta-blockers like propranolol or carvedilol. Active therapy of acute bleeding may be based on three strategies: vasopressor drugs like terlipressin, antibiotics and cyanoacrylate. Biecker E., (2013) "Portal hypertension and gastrointestinal bleeding: diagnosis, prevention and management" *World J Gastroenterol.* 19(31):5035-5050.

Portal hypertension is usually determined by means of an HVPG, the value of which closely correlates with that of the portacaval pressure gradients. In healthy adults, HVPG values are nominally within the range 1-5 mmHg. An HVPG value of 6-9 mmHg corresponds to preclinical sinusoidal portal hypertension, whereas clinically significant portal hypertension is diagnosed when HVPG is ~10 mmHg, at which point clinical manifestations of portal hypertensive syndrome, such as varices, bleeding, gastropathy, and ascites, might appear.

Portal hypertension may develop as a result of any condition that interferes with blood flow within the portal system can cause portal hypertension, so this condition is classified according to the site of obstruction as prehepatic (involving the splenic, mesenteric, or portal veins), intrahepatic (parenchymal liver diseases) and posthepatic (diseases involving the hepatic venous outflow.

B. Chronic Viral Hepatitis

Hepatitis is generally observed as a swelling and inflammation of the liver which can be caused by infections from viruses (such as hepatitis A virus, hepatitis B virus, or hepatitis C virus). Hepatitis may present as an acute condition where it develops and recovers quickly. However, hepatitis may also become a long-term (e.g., chronic) condition. In some cases, chronic hepatitis may lead to liver damage, liver failure, or even liver cancer.

Symptoms of hepatitis generally include, but are not limited to, pain or bloating in the belly area, dark urine and pale or clay-colored stools, fatigue, low fever, itching, jaundice (yellowing of the skin or eyes), loss of appetite, nausea and vomiting, and/or weight loss. In some types of hepatitis there is no known treatment (e.g., hepatitis A), but patients usually recover within six months. However, chronic hepatitis B or C infections may be treated with peginterferon or antiviral drugs. Antiviral drugs can decrease or remove hepatitis B or C from the blood as well as reduce the risk of cirrhosis and/or liver cancer.

The usual evaluation parameters for chronic hepatitis include, but are not limited to, transaminase levels, viral kinetics, and/or liver biopsy. Nonetheless, changes in HVPG can be useful for staging chronic hepatitis and for evaluating the response of the disease to antiviral treatment. HVPG is believed to reflect liver parenchymal function as does liver biopsy. Burroughs et al., "Assessment of therapeutic benefit of antiviral therapy in chronic hepatitis C: is hepatic venous pressure gradient a better end point?" *Gut* 50:425-421 (2002). Consistent with this view, HVPG relates with a degree of histological liver fibrosis in patients with HBV-related and HCV-related chronic hepatitis. HVPG is over 5 mmHg in the majority of patients with significant fibrosis (e.g., stage≥F2; according to the Metavir scoring system). Kumar et. al., "Hepatic venous pressure gradient as a predictor of fibrosis in chronic liver disease because of hepatitis B virus" *Liver Int.* 28:690-698 (2008).

C. Acute Alcoholic Hepatitis

Acute alcoholic hepatitis is generally defined as any damage to the liver and its function due to alcohol abuse that occurs after years of heavy drinking Alcohol can cause inflammation in the liver, and over time, results in scarring and cirrhosis (the final phase of alcoholic liver disease).

Symptoms vary and can be categorized into several groups including, but not limited to: i) Digestive symptoms: pain and swelling in the abdomen, decreased appetite and weight loss, nausea and vomiting, fatigue, dry mouth and increased thirst, bleeding from enlarged veins in the walls of the lower part of the esophagus; ii) Epidermal symptoms: yellow color in the skin, mucus membranes, or eyes (jaundice), small, red spider-like veins on the skin, very dark or pale skin, redness on the feet or hands, itching; and iii) Neurological symptoms: problems with thinking, memory, and mood, fainting and lightheadedness and/or numbness in the extremities.

Treatment usually focuses upon cessation of alcohol consumption to facilitate hepatic healing and recovery. However, malnutrition generally accompanies the conditions that is treated with the administration of total parenteral nutrition compounds that includes but is not limited to amino acids, vitamins (e.g., for example, B-complex vitamins and folic acid).

Acute alcoholic hepatitis (AAH) is a severe condition with high mortality. In patients with alcoholic cirrhosis, the presence of AAH is associated with elevated HVPG values, which suggests that the inflammatory state of this condition contributes to increased portal pressure. In patients with severe AAH, HVPG (when measured early during hospitalization) provides prognostic information on short-term outcomes; values >22 mmHg were independently associated with a higher risk of death than were values below this threshold. Sen et al., "Albumin dialysis reduces portal pressure acutely in patients with severe alcoholic hepatitis" *J. Hepatol.* 43:142-148 (2005); and Rincon el al., "Prognostic value of hepatic venous pressure gradient for in-hospital mortality of patients with severe acute alcoholic hepatitis" *Aliment. Pharmacol. Ther.* 25:841-848 (2007).

D. Liver Transplantation

Liver transplantation is generally considered to be any surgery that replaces a diseased liver with a healthy liver. The healthy liver is provided by a donor individual who has either recently died or a healthy (living) individual provides a partial liver, as the transplanted liver tissue will regrow to is full size. The transplant procedure is now routine (~12 hours in duration), where the donated liver is removed from the donor through a surgical cut in the upper abdomen and is placed into the recipient individual, followed by attachment of the blood vessels and bile ducts.

To avoid tissue rejection, almost all transplant recipients must take medicines that suppress their immune response for the rest of their lives. This is called immunosuppressive therapy that comprises the administration of immunosuppressive drugs. Although the treatment helps prevent organ rejection, it also puts people at a higher risk for infection and cancer because the drug lower the body's resistance.

In patients who underwent liver transplantation for HCV-related cirrhosis, HVPG values and liver biopsy may identify patients who are at highest risk of undergoing decompensation from recurrence of severe hepatitis C. For example, fibrosis often develops with a peri-sinusoidal pattern, which leads to inaccurate staging when scoring systems are used. For example, patients classified as Metavir stage F2 had HVPG measurements >10-12 mmHg. For this reason, HVPG may be able to assess chronic viral hepatitis recurrence after orthotopic liver transplantation. Further, the presence of portal hypertension at 12 months after orthotopic liver transplantation, as indicated by an HVPG value 2.6 mmHg, enabled the identification of patients with rapid deterioration of liver function and recurrence of cirrhosis. Blasco et al., "Hepatic venous pressure gradient identifies patents at risk of severe hepatitis C recurrence after liver transplantation" *Hepatology* 43:492-499 (2006); Carrion et al., "Transient elastography for diagnosis of advanced fibrosis and portal hypertension in patient with hepatic C recurrence after liver transplantation" *Liver Transpl.* 12:1791-1798 (2006); Samonakis et al., "Hepatic venous pressure gradient to assess fibrosis and its progression after liver transplantation for HCV cirrhosis" *Liver Transpl.* 13: 1305-1311 (2007); and Kalambokis et al., "Clinical outcome of HCV-related graft cirrhosis and prognostic value of hepatic venous pressure gradient" *Transpl, Int.* 22: 172-181 (2009). Serial HVPG measurements showed a similar improvement in condition to that seen by liver histology in liver transplant recipients who responded to antiviral therapy. Carrion et al., "Efficacy of antiviral therapy on hepatitis C recurrence after liver transplantation: a randomized controlled study" *Gastroenterology* 132: 1746-1756 (2007).

E. Hepatocellular Carcinoma

Hepatocellular carcinoma (HCC) is a common malignancy on a worldwide basis. Different signaling pathways have been identified to be implicated in the pathogenesis of HCC; among these, growth hormone (GH), insulin-like growth factor (IGF) and somatostatin (SST) pathways have emerged as pathways implicated in the development of HCC. Physiologically, the GH-IGF-SST system plays a role in liver growth and development since GH induces IGF1 and IGF2 secretion and the expression of their receptors, involved in hepatocytes cell proliferation, differentiation and metabolism. On the other hand, somatostatin receptors (SSTRs) are usually associated with the biliary tract. The GH-IGF-SST system components have also been indicated as regulators of hepatocarcinogenesis. For example, reduction of GH binding affinity to GH receptor, decreased serum IGF1 and increased serum IGF2 production, overexpression of IGF1 receptor, loss of function of IGF2 receptor and appearance of SSTRs are frequently observed in human HCC. In particular, recently, many studies have evaluated the correlation between increased levels of IGF1 receptors and liver diseases and the oncogenic role of IGF2 and its involvement in angiogenesis, migration and, consequently, in tumour progression. SST directly or indirectly influences tumour growth and development through the inhibition of cell proliferation and secretion and induction of apoptosis, even though SST role in hepatocarcinogenesis is still opened to argument. Several approaches to GH-IGF-SST system targeting have been used as novel therapeutic strategies in HCC, and some others are currently under evaluation. Generally, molecular therapeutic strategies include the use of antibodies, which can have anti-ligand and/or anti-receptor activity, the use of small molecules inhibitors, which can interfere with key enzymatic functions, and the use of synthetic receptor agonists or antagonists. All these approaches can interfere with cell proliferation and/or, specifically, with apoptosis. Monoclonal antibodies and small molecule inhibitors can be used to target receptors, particularly growth factor-RTK. These growth factor-RTK targeting approaches can be combined with different small molecule inhibitors targeting cytoplasmic oncogenic kinases. Several compounds have been reported to treat HCC. See, Table 1.

TABLE 1

Currently available agents for the treatment of HCC

| Compound 1 | Company | Mechanism of action | Intervention | Type of Cancer |
|---|---|---|---|---|
| MEDI-573 | MedImmune LLC | Fully Human mAb anti-IGF1 and -IGF2 | In combination with sorafenib | Unresectable or metastatic HCC |
| IMC-A12 | National Cancer Institute | Fully Recombinant Human mAb anti-IGF1R | Alone | Adult Primary, advanced, localized unresectable, recurrent HCC |
| | National Cancer Institute | | In combination with sorafenib tosylate | Advanced HCC |
| | Eli Lilly and Company | | In combination with sorafenib | Advanced HCC |
| BIIB-022 | BiogenIdec | Human IgG4P nonglycosylated antibody anti-IGF1R | In combination with sorafenib | Advanced HCC |
| AVE-1640 | Sanofi-Aventis | Humanized mAb anti-IGF1R | Alone and in combination with sorafenib and erlotinib | HCC not eligible for local treatment |
| OSI-906 | AstellasPharmaInc | Small molecule inhibitor of IGF1R | Alone | With advanced HCC after failure of first-line treatment with sorafenib |

Data from clinicaltrials.gov.

Drugs targeting the IGF1R are also called IGF1R-blockers and include: anti IGF1R monoclonal antibodies such as CP-751,871, AVE1642/EM164, IMC-A12, SCH-717454, BIIB022, AMG 479 and MK-0646/h7C10, and small molecules RTK inhibitors such as OSI-906. IMC-A12, also known as cixutumumab, is a fully human monoclonal IgG1 antibody that binds IGF with high affinity, inhibits ligand-dependent receptor activation and downstream signaling, and also mediates IGF1R internalization and degradation. IMC-A12 has shown antitumoral activity against a wide range of human tumour types in in vitro studies. The effect of IMC-A12 has been evaluated in human breast (MCF7), pancreas (BxPC-3), and colon (Colo205) carcinoma cell lines, in which the antibody inhibits cell proliferation and induces cell apoptosis. In the same study, IMC-A12 has also shown activity against a human tumour in both in vivo xenograft and orthotopic models.

SSTRs are a treatment target in some types of tumours. Given the short half-life of native SST, several synthetic somatostatin analogues (SA) have been developed and are currently used in clinical practice, mainly to treat patients with neuroendocrine tumours (NET). Currently reports SAs include, but are not limited to: octreotide, which binds with high affinity to SSTR2 and with reduced affinity to SSTR3 and SSTR5; lanreotide, which primarily binds with high affinity to SSTR2 but shows reduced or no binding to SSTR1, 3, 4 and 5 subtypes; pasireotide, which has high affinity for SSTR5 but it also binds SSTR2, SSTR3 and SSTR1, with decreased affinity. Several in vitro studies using cell lines transfected with SSTRs indicate that all receptor subtypes (SSTR1-5) may mediate the inhibition of cell proliferation, whereas specific receptor subtypes (SSTR2, SSTR3) may mediate the induction of apoptosis. These effects are regulated primarily via MAPK pathway and through the activation of phosphotyrosine phosphatases. The growth inhibition effects of SA might be also induced by the restoration of functional gap junctions. Moreover, SA could upregulate the tumour suppressor protein p53 and activate the pro-apoptotic member of the Bcl-2 protein family, Bax, thus triggering apoptosis. Pivonello et al., (2014) "The GH-IGF-SST system in hepatocellular carcinoma: biological and molecular pathogenetic mechanisms and therapeutic targets" *Infect Agent Cancer* 20:9-27.

In a secondary analysis of a randomized, controlled trial in patients with compensated cirrhosis, HVPG, in addition to albumin levels and viral etiology, were independent predictors of the risk of developing hepatocellular carcinoma. Roberts et al., "Effect of sustained viral response on hepatic venous pressure gradient in hepatitis c-related cirrhosis" *Clin. Gastroenterol. Hepatol.* 5:932-937 (2001). This risk is substantially higher in patients with clinically significant portal hypertension (HVPG 2-10 mmHg) than in patients with cirrhosis who have HVPG values <10 mmHg. Similarly, in patients with well-compensated cirrhosis and resectable hepatocellular carcinoma, the presence of clinically significant portal hypertension markedly increases the risk of unresolved hepatic decompensation occurring within 3 months of hepatic resection. Bruix et al., "Surgical resection of hepatocellular carcinoma in cirrhotic patients: prognostic value of preoperative portal pressure" *Gastroenterology* 111: 1018-1022 (1996); Liovet et al., "Intention-to-treat analysis of surgical treatment for early hepatocellular carcinoma: resectin versus transplantation" *Hepatology* 30:1434-1440 (1999); and Forner et al., "East meets the West—portal pressure predicts outcome of surgical resection for hepatocellular carcinoma" *Nat. Clin. Pract. Gastrenterol. Hepatol.* 6: 14-15 (2009).

F. Cirrhosis

Cirrhosis is generally defined as a scarring of the liver and poor liver function and is usually the last stage of chronic liver disease. Cirrhosis may have causative factors including, but not limited to, hepatitis B or C infection, alcohol abuse, autoimmune hepatitis, bile duct disorders, medicines, hereditary diseases, other liver diseases, such as nonalcoholic fatty liver disease (NAFLD) and nonalcoholic steatohepatitis (NASH).

There may be no symptoms, or symptoms may come on slowly, depending on how well the liver is working. For example: early symptoms may include, but are not limited to: fatigue and loss of energy, poor appetite and weight loss, nausea or belly pain, small, red spider-like blood vessels on the skin; chronic symptoms may include, but are not limited to: fluid buildup of the legs (edema) and in the abdomen (ascites), yellow color in the skin, mucus membranes, or eyes (jaundice), redness on the palms of the hands, male sex organ dysfunction (e.g., for example, impotence, shrinking of the testicles, and/or breast swelling), easy bruising and abnormal bleeding, confusion or problems thinking, and/or pale or clay-colored stools.

Aside from lifestyle changes, treatment may include the administration of therapeutic drugs including, but not limited to, diuretics, vitamin K, neurocognitive agents, and/or antibiotics.

HVPG is a strong and independent predictor of several outcomes in patients with cirrhosis. Cross-sectional studies that addressed correlations between clinical and hemodynamic parameters have shown that clinically significant portal hypertension is necessary for gastroesophageal varices to form and bleed. Lebrec et al., "Portal hypertension, size of esophageal varicies, and risk of gastrointestinal bleeding in alcoholic cirrohosis" *Gastroenterology* 79:1139-1144 (1980). This link has been confirmed in a prospective, randomized trial carried out in patients with compensated cirrhosis who had no esophageal varices at inclusion. The results showed that the presence of clinically significant portal hypertension is a major determinant of such patients' prognosis, and indicates an increased risk of developing varices, first decompensation, and hepatocellular carcinoma. In patients who had already developed decompensation, HVPG provided information about the risk of death during follow•up. Merkel et al., "Prognostic usefulness of hepatic vein catheterization in patients with cirrhosis and esophageal varices" *Gastroenterology* 102: 973-979 (1992); Vorobioff et al., "Prognostic value of hepatic venous pressure gradient measurements in alchology cirrhosis: a 10-year prospective study" *Gastroenterology* 111: 701-709 (1996); and Gluud et al., "Prognositic indicators in alcoholic cirrhotic men" *Hepatology* 8:222-227 (1988). 16 mmHg was the optimum cut-off value for this correlation. On the basis of this evidence, current guidelines recommend the measurement of HVPG as soon as cirrhosis is diagnosed to help stratify patients' risk. De Franchis, R., "Evolving consensus in portal hypertension: report of the Baveno IV consensus workshop on methodology of diagnosis and therapy in portal hypertension" *J. Hepatol.* 43:167-176 (2005); and Garcia-Tsao et al., Portal hypertension and variceal bleeding—unresolved issues: summary of an American Association for the Study of Liver Diseases and European Association for the Study of Liver Diseases and European Association for the Study of the Liver single-topic conference" *Hepatology* 47:1764-1772 (2008).

G. Hepatic Embolization

Embolisms may occur in the hepatic circulatory system, most notably the hepatic portal vein. Treatment of embolisms and/or thrombosis generally use anticoagulant drugs including, but not limited to, heparin, coumadin, warfarin. Reports have also recommended other therapies both for the treatment and/or prevention of hepatic thrombosis. For example, aspirin alone may be used for thromboprophylaxis of any patient group. Alternatively, a low-dose unfractionated heparin (LDUH) (5,000 U bid) or low-molecular-weight heparin (LMWH) [< or =3,400 U once daily] may achieve thromboprophylaxis. Alternatively, three other anticoagulant agents, LMWH, fondaparinux, or adjusted-dose vitamin K antagonist (VKA) may also provide thromboprophylaxis. Geerts et al., "Prevention of venous thromboembolism: the Seventh ACCP Conference on Antithrombotic and Thrombolytic Therapy" *Chest* (2004) 126(3 Suppl): 338S-400S.

Thrombosis of the portal venous system is a frequent and potentially life-threatening condition that can take place in a number of different clinical settings including liver cirrhosis, hepatocellular carcinoma, other solid tumours, abdominal septic foci, acute pancreatitis, haematological malignancies and congenital or acquired prothrombotic disorders. Clinical decision-making in patients with thrombosis of the portal venous system is a particularly complex process owing to the heterogeneity of the population affected by this condition and the lack of high-quality evidence from randomized controlled trials for the use of anticoagulation therapy in these patients. Imaging can facilitate a decision-making process in different clinical settings. Berzigotti et al., "Imaging in clinical decision-making for portal vein thrombosis" Nat Rev Gastroenterol Hepatol. (2014) 11(5):308-316.

Occlusive portal vein thrombosis (PVT) is common complication of chronic liver disease with prevalence ranging from 1% to 16% of population. The occurrence of portal vein thrombosis is influenced by local factors (cirrhosis with associated liver architectural changes and increased resistance effects), systemic factors (inherited and acquired abnormalities leading to hyper coagulability) and development of hepatocellular carcinoma. The majority of patients with cirrhosis PVT are diagnosed on radiographic studies although in some patients PVT may present with decompensated chronic liver disease but the natural history of PVT in patients with cirrhosis is largely unknown. However patients with cirrhosis and PVT have been shown to have inferior survival in comparison with patients without PVT. Debnath et al. "Cirrhosis of liver and portal vein thrombosis—a review article" Mymensingh Med J. (2014) 23(3): 606-608.

Portal vein tumor thrombosis (PVTT) is a common paraneoplastic condition in advanced primary hepatocellular carcinoma or hepatobiliary tract malignancies. Tumors with PVTT are frequently associated with adverse and aggressive features such as intrahepatic tumor dissemination, early treatment failure, or deterioration of hepatic function. Therefore, the treatment outcomes for PVTT in historical series are often dismal and discouraging. More recently, beneficial effects and excellent outcomes of external beam radiation therapy (EBRT) for treating this disease have been reported, and the use of EBRT is becoming more common because of the non-invasive nature of RT and rapid advances in RT technology. We hope to be able to cure this devastating condition in the near future with more advanced and efficacious disease management strategies. The current status and clinical trial results for EBRT as a promising treatment option for managing PVTT will be discussed here. Lee et al., "Radiotherapeutic options for hepatocellular carcinoma with portal vein tumor thrombosis" Liver Cancer (2014) 3(1): 18-30.

VI. Hepatic Imaging

Imaging of the liver has progressed rapidly during the past decade with continued advancement of current ultrasound, computed tomography, and magnetic resonance imaging (MRI). Each modality not only has seen refinement enabling better anatomic characterization of disease but also has received strength from the addition of new techniques to its resources. New contrast agents have become available for all modalities and some agents, particularly for MRI, have opened the way for better functional assessment. MRI continues to see an elaboration of sequences (including spectroscopy and diffusion) that also open imaging to the microscopic structure of disease and normal function. The further development of workstations have improved both analysis and depiction of disease. In the 21st century imaging will continue to shift from a simple source of anatomic information to a more functional problem-solving tool. Cohen et al., "Hepatic imaging in the 21st century" Semin Liver Dis. (2006) 26(4):363-372.

Commonly employed hepatic imaging diagnostic techniques include ultrasound, computerized tomography, magnetic resonance, and positron emission tomography. While useful, these techniques have specific limitations to fully evaluate many hepatic disorders including, but not limited to, liver metastases, HCC, RF ablation recovery and/or liver transplantation success evaluation. Braga et al., "Modern hepatic imaging" Surg Clin North Am. (2004) 84(2):375-400.

It is known that to obtain optimal detection and characterization of focal or diffuse liver disease, imaging tests need to be selected in the context of the correct clinical setting. For example, patient clinical information and medical history should be considered in the context of one's familiarity with currently available modalities for imaging the liver. Such consideration allows the optimal use of the technical advances in ultrasound imaging, CT scanning, MR imaging, and nuclear scintigraphy technology and contributes to improved diagnostic accuracy. Ros et al., (2002) "Hepatic imaging. An overview" Clin Liver Dis. 6(1):1-16.

In some embodiment, the limitations of conventional hepatic imaging techniques can be overcome by combining a portal venous access catheter, as disclosed herein, with endoscopic imaging. For example, an endoscopic imaging device can be inserted into a portal venous access catheter for improved imaging of a variety of hepatic disorders as discussed herein.

VII. Pharmacodynamic And Pharmacokinetic Studies

In one embodiment, the present invention contemplates a method to perform pharmacodynamic and/or pharmacokinetic studies and/or drug monitoring. For example, the method measures first pass hepatic metabolism of compounds including, but not limited to, drugs, vitamins, hormones, amino acids etc. In one embodiment, the monitoring is performed using a portal access catheter. In one embodiment, the portal access catheter may infuse a compound into a portal vein. In one embodiment, the portal access catheter collects a hepatic vein blood sample.

Pharmacodynamics (PD) is the study of: i) biochemical and physiological effects of compounds; ii) compound mechanisms of action; and iii) relationships between compound concentration and effects. Lees et al., (2004) "Principles of pharmacodynamics and their applications in veterinary pharmacology" J. Vet. Pharmacol. Ther. 27(6):397-414. Such physiological effects may include, but are not limited to, that that: a) mimic or inhibit normal physiological/biochemical/pathological processes; b) inhibit vital processes of endo- or ectoparasites and microbial organisms. Compound mechanisms of action may include, but are not limited to: a) stimulating action through direct receptor agonism; b) inhibiting action through direct receptor agonism; c) inhibiting action through a receptor stabilizing action; d) direct exchange or replacement of naturally occurring substances; e) free radical scavenging; f) cellular damage or destruction (e.g., for example, cytotoxicity or irritation); g) cellular membrane disruption; h) chemical reactions; i) enzyme interactions; j) protein interactions; k) ion channel interactions, and/or l) receptor/ligand binding interactions. PD also encompasses the determination of therapeutic windows and/or durations of action. A therapeutic window can be an amount of a medication between the amount that gives an effect (effective dose) and the amount that gives more adverse effects than desired effects. For instance, a medication with a small pharmaceutical window must be administered with care and control, e.g. by frequently measuring blood concentration of the drug, since it easily loses effects or gives adverse effects. A duration of action of a compound is the length of time that particular drug is effective. Duration of action is a function of several parameters including plasma half-life, the time to equilibrate between plasma and target compartments, and the off rate of the drug from its biological target.

Pharmacokinetics (PK) can determine the fate of substances administered externally to a living organism. These substances of interest include, but are not limited to, pharmaceutical agents, hormones, nutrients, and toxins. PK attempts to discover the fate of a drug from the moment that it is administered up to the point at which it is completely eliminated from the body. Pharmacokinetics describes how the body affects a specific drug after administration through the mechanisms of absorption and distribution, as well as the chemical changes of the substance in the body (e.g. by metabolic enzymes such as cytochrome P450 or glucuronosyltransferase enzymes), and the effects and routes of excretion of the metabolites of the drug. Pharmacokinetic properties of drugs may be affected by elements such as the site of administration and the dose of administered drug. These may affect the absorption rate. Kathleen Knights; Bronwen Bryant (2002). In: Pharmacology for Health Professionals. Amsterdam: Elsevier. ISBN 0-7295-3664-5. A number of different PK models have been developed in order to simplify conceptualization of the many processes that take place in the interaction between an organism and a drug. One of these models, the multi-compartment model, gives a generally accepted practical approximation. However, monocompartmental models and two compartmental models are more frequently used because of reduced computational complexity. For example, PK generally contemplates that metabolism is compartmentalized and is commonly referred to as ADME: i) Liberation—the process of release of a drug from the pharmaceutical formulation; ii) Absorption—the process of a substance entering the blood circulation: iii) Distribution—the dispersion or dissemination of substances throughout the fluids and tissues of the body; iii) Metabolization (or biotransformation, or inactivation)—the recognition by the organism that a foreign substance is present and the irreversible transformation of parent compounds into daughter metabolites; and iv) Excretion—the removal of the substances from the body. Metabolism and Excretion compartment are sometimes grouped together under for form an Elimination compartment. PK is generally a calculation based upon mathematical formulas that have a corresponding graphical representation. The use of these models allows an understanding of the characteristics of a molecule, as well as how a particular drug will behave given information regarding some of its basic characteristics. Such as its acid dissociation constant (pKa), bioavailability and solubility, absorption capacity and distribution in the organism. PK model outputs can be used in industry (for example, in calculating bioequivalence when designing generic drugs) or in the clinical application of pharmacokinetic concepts. Clinical pharmacokinetics provides many performance guidelines for effective and efficient use of drugs for human-health professionals and in veterinary medicine.

I claim:

1. A direct portal vein access catheter device comprising a catheter body having a proximal end, a distal end, a main lumen, wherein said main lumen extends from said proximal end to said distal end, and a balloon-fill lumen, wherein said balloon-fill lumen extends from a balloon-fill hub to an anchor balloon, wherein said anchor balloon is insertable into a portal vein and inflatable to engage said portal vein and prevent dislodgement; a subcutaneous connection hub at said proximal end comprising an infusion lumen port connected to said main lumen and said balloon-fill hub, and a connector that interfaces said main lumen to said infusion lumen port and said balloon-fill lumen to said balloon-fill hub.

2. The device of claim 1, wherein said catheter body is further configured with a tissue penetrator.

3. The device of claim 1, wherein said device further comprises an imaging apparatus attached to said catheter body.

4. The device of claim 1, wherein said anchor balloon is contained at said distal end of said catheter body.

5. The device of claim 1, wherein said catheter body is surrounded by a hemostatic clamp.

6. The device of claim 1, wherein said catheter body is surrounded by a ring slide for securing the catheter body proximal end to the subcutaneous connection hub.

7. The device of claim 1, wherein said catheter body has an initial length that is cut to size for a given patient.

8. The device of claim 1, wherein said connector further comprises a metal connector.

9. The device of claim 8, wherein said subcutaneous connection hub is removable.

10. The device of claim 9 further comprising a ring slide about said catheter body for securing the catheter body proximal end to the metal connector.

11. The device of claim 8, further comprising a hemostatic clamp mounted about the catheter body, said hemostatic clamp having a closed state to prevent a flow through said main lumen when said subcutaneous connection hub is not connected.

12. The device of claim 1, wherein said infusion lumen port is configured perpendicular in relation to said balloon-fill hub.

13. The device of claim 1, wherein the catheter body further comprises a central venous lumen having a proximal end connected to said subcutaneous connection hub, and a terminal end located between said main lumen distal end and said proximal end.

14. The device of claim 13, wherein said central venous lumen terminal end is approximately 12 cm from the catheter body distal end.

15. The device of claim 13, wherein the subcutaneous connection hub infusion lumen port further comprises a first infusion lumen connected to said main lumen, and a second infusion lumen connected to said central venous lumen, and said balloon-hub connected to said balloon-fill lumen.

16. The device of claim 15, further comprising a metal connector interposed between said subcutaneous connection hub and said catheter interfacing said central venous lumen to said first infusion lumen, said main lumen to said second infusion lumen, and said balloon-fill lumen to said balloon-fill hub, wherein the subcutaneous connection hub is removable.

17. The device of claim 15, further comprising a hemostatic clamp mounted about the catheter body, said hemostatic clamp having a closed state to prevent a flow through said main lumen when said subcutaneous connection hub is not connected.

18. The device of claim 1 wherein said main lumen does not overlap said balloon-fill lumen.

* * * * *